United States Patent [19]

Anderson

[11] 4,168,233

[45] Sep. 18, 1979

[54] AUTOMATIC ACTIVATED SLUDGE CONTROL SYSTEM

[75] Inventor: James J. Anderson, Marine-on-St. Croix, Minn.

[73] Assignee: Watermation, Inc., St. Paul, Minn.

[21] Appl. No.: 934,201

[22] Filed: Aug. 16, 1978

[51] Int. Cl.$^2$ .............................................. B01D 21/24
[52] U.S. Cl. ........................................ 210/86; 210/94; 210/96.1; 210/104; 210/112; 210/197
[58] Field of Search ................... 210/85, 86, 94, 96 R, 210/97, 112, 197, 294, 104

[56] References Cited

U.S. PATENT DOCUMENTS

| | | | |
|---|---|---|---|
| 2,709,680 | 5/1955 | Watson | 210/97 |
| 3,746,167 | 7/1973 | Arthur | 210/86 |
| 3,837,216 | 9/1974 | Shinohara | 210/86 |
| 4,130,481 | 12/1978 | Chase et al. | 210/96 R |

*Primary Examiner*—John Adee
*Attorney, Agent, or Firm*—Neil B. Schulte

[57] ABSTRACT

A system for automatically extracting samples of sludge and mixed liquor from a sewage treatment plant, delivering them to a testing settleometer jar and centrifuge and measuring the rate of settling of sludge and suspended solids in the test samples.

9 Claims, 4 Drawing Figures

AUTOMATIC ACTIVATED SLUDGE CONTROL SYSTEM

BACKGROUND OF THE INVENTION

The proper and efficient operation of a sewage treatment plant is dependent upon the rate at which activated return sludge is cycled in the system. The return sludge carries the necessary operating bacteria back into the system to control the rate of treatment. The best operation is obtained when one knows continuously the condition of the return sludge which is determined by measuring the amount of solids suspended in the fluid and the settling rate of the activated sludge. In the prior art the only known way to determine these factors involves a manual test in which an operator must take a sample of the sludge and the mixed liquor and run them through a prolonged settling test in which the amount of solids and the settling rate are observed by eye and recorded by hand. This operation is slow and expensive since it requires the labor of the operator. Frequently the tests simply are not performed often enough to maintain a good operating picture of the system and consequently the sewage plant never quite operates at its optimum level but is always in the process of being corrected back from extreme conditions of too much or too little activated sludge. The present invention corrects these difficulties.

SUMMARY OF THE INVENTION

Briefly, my invention comprises an automatic sampling system which operates without an operator to sample the activated sludge and the mixed liquor and determine the relevant ratios of activated sludge and solids to provide either a printed record or an automatic control signal which can control the return sludge flow rate. The arrangement of the valves, testing equipment, control circuits, and readouts is described in detail hereinafter. However, the main advantages of my invention include a low cost operation which results from freeing the operator from routine manual tests and plant adjustments. Also, if the testing is done continuously, trends can be established and process upsets detected at an early stage so that correcting adjustments can be introduced before the sewage treatment facility reaches an extreme condition of imbalance. The optical readout mechanisms utilized in the present invention are highly accurate and therefore less prone to errors found in the prior art visual checks. The rugged construction can be simply maintained and eliminates the necessity of specialized service so that the plant operators can maintain the machinery themselves. No manual adjustments are necessary and the system is completely automatic providing a printed record that can be used by operators of ordinary skill.

It may therefore be seen that it is an object of my invention to provide an automatic activated sludge control system for sewage treatment plants which provides improved operation through lower cost, more accurate control, and elimination of the need for highly skilled operators. Further objects and advantages will become apparent from the following detailed description and drawings.

DESCRIPTION OF THE PREFERRED EMBODIMENT

Figure 1:
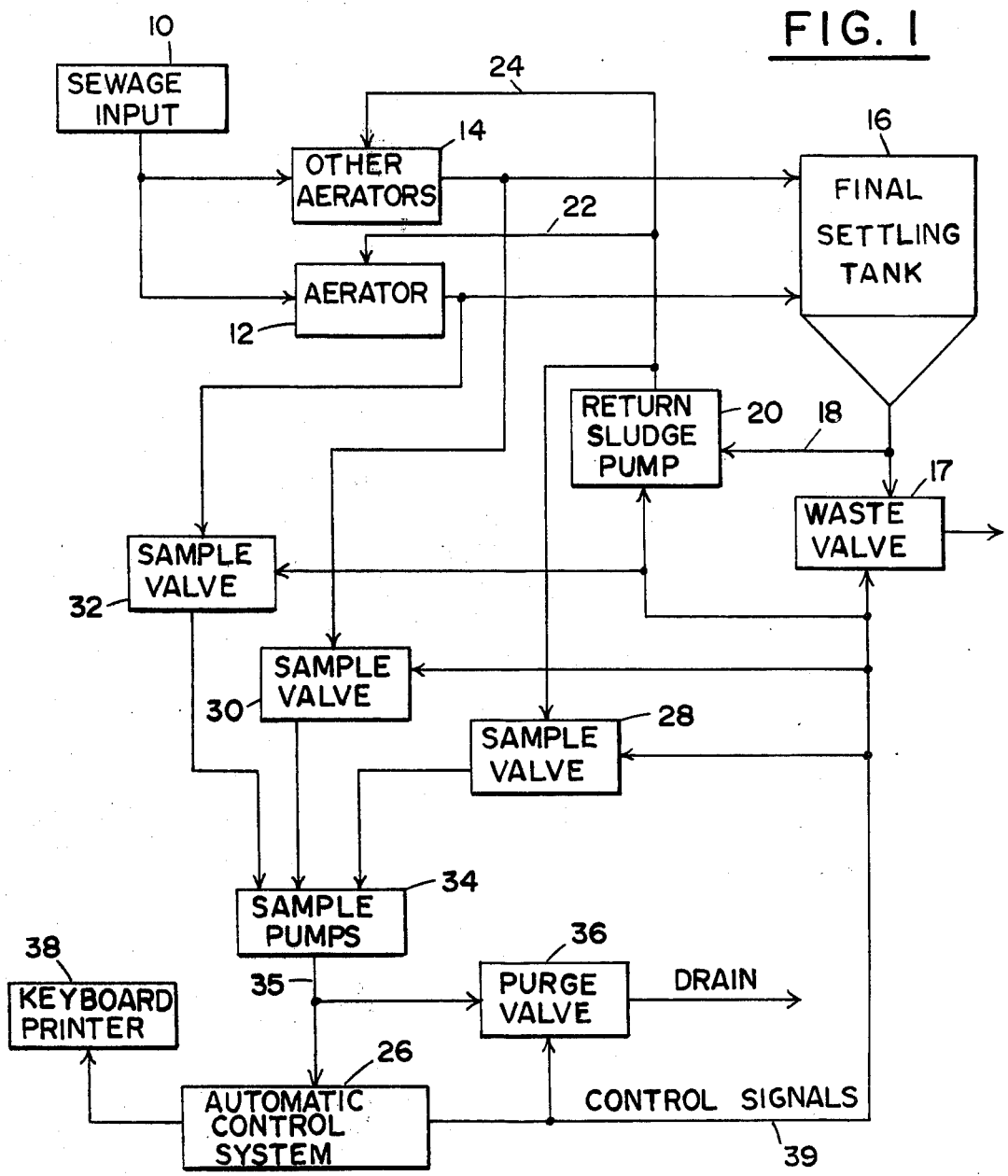
FIG. 1 is a schematic flow diagram showing how the automatic control system of the present invention operates in conjunction with a typical sewage treatment facility.

In FIG. 1 the sewage input 10 is directed to an aerator tank 12 in which the activated sludge and mixed liquor are continuously circulated with air to maintain the treatment process. Additional aerator tanks 14 may also be used depending upon the size of the facility. The treated effluent is drawn off to a final settling tank 16 where the sludge settles out to eventually be discharged through a waste valve 17. This sludge contains the necessary bacteria to maintain the treatment operation and a portion of it may be returned through line 18 by a return sludge pump 20 to the aerator tanks 12 and 14. The amounts of waste and return sludge primarily determine if the process in the aerator tanks is proceeding efficiently. With the present invention the fluid in the aerator tanks 12 and 14 can be delivered to an automatic control system 26 by means of sample valves 30 or 32 and sample pumps 34. The return sludge is sampled through a valve 28. The result of the testing can be displayed on a keyboard printer 38 or used to develop control signals 39 to operate the return sludge pump 20 and the waste valve 17. Before samples are tested, the line 35 from the treatment facility is purged through a purge valve 36 as will be explained with respect to FIG. 4.

Figure 2:
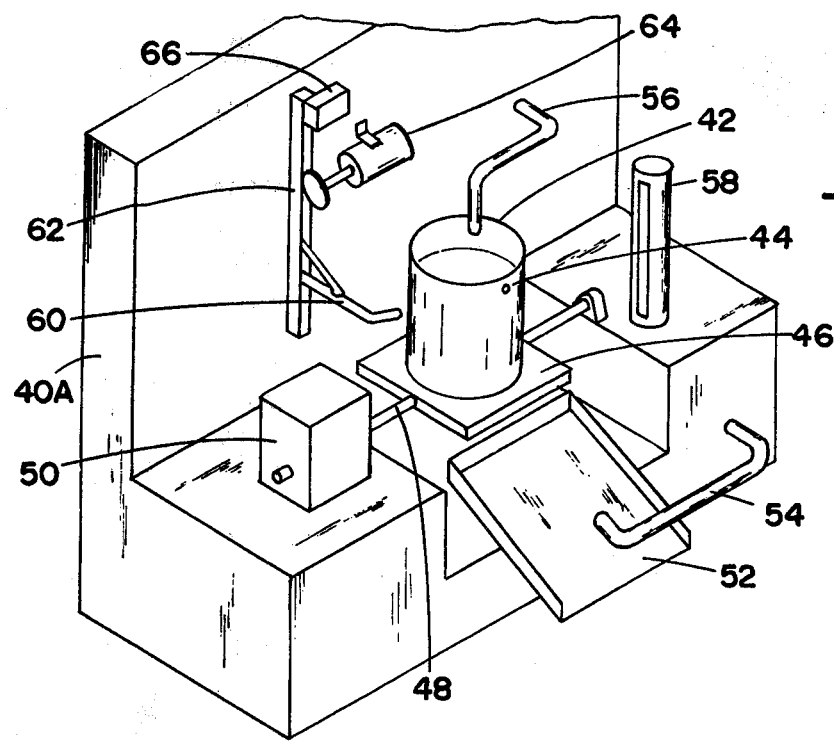
FIGS. 2 and 3 show the two halves of the testing station with the settleometer jar test and the centrifuge test respectively.
Figure 3:
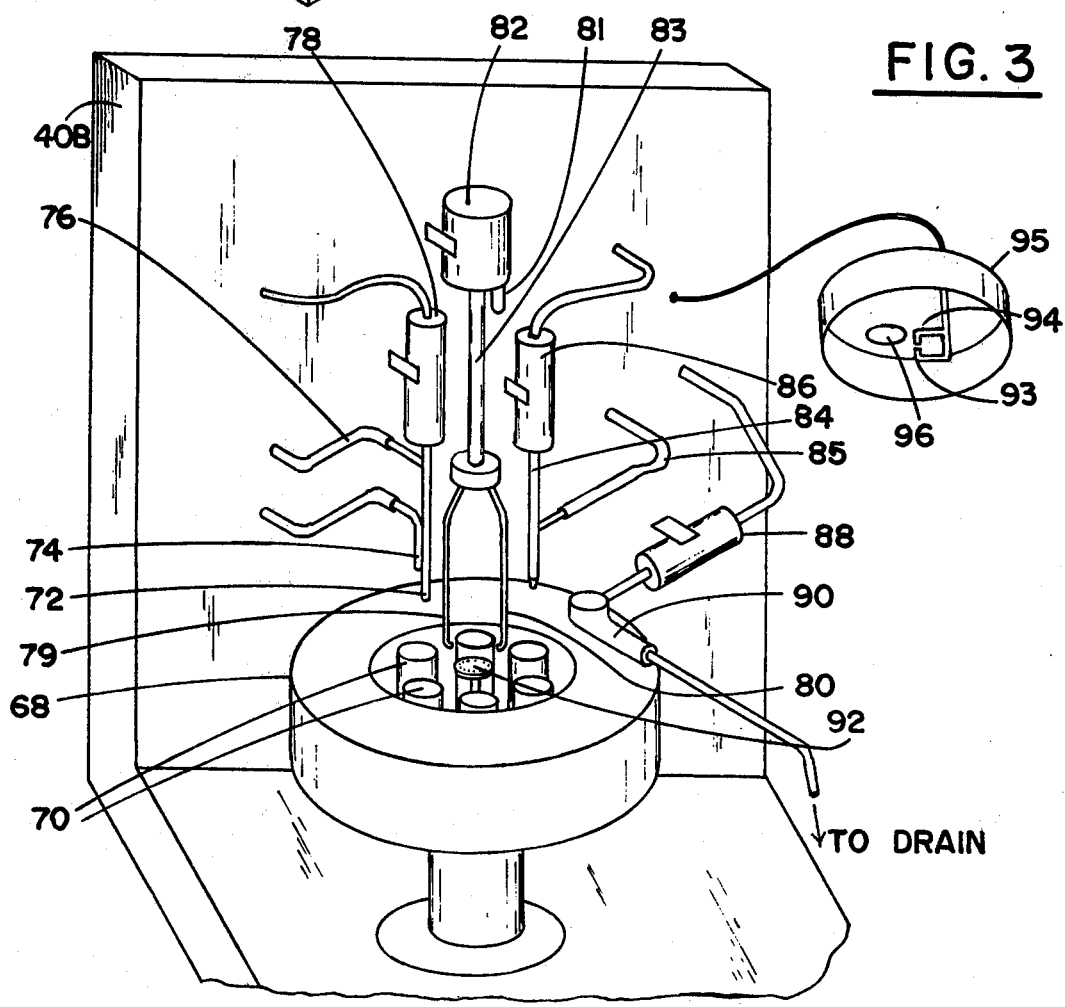

Basically, two tests are performed by the present invention. The aerator tank mixed liquor is directed to a settleometer jar 42 shown in FIG. 2 and allowed to settle. The mixed liquor and the return sludge are directed to a centrifuge 68 and caused to forcibly settle out to determine the ratio of solids therein. The centrifuge 68 is shown in FIG. 3. However, it is contemplated that both portions of the testing apparatus will be mounted on a common testing station console which is divided into console 40A in FIG. 2 and 40B in FIG. 3 for the sake of clarity in the drawings. The settleometer jar 42 in FIG. 2 is filled through a fill pipe 56. An overflow hole 44 ensures that jar 42 will be filled to a precise level from which one can accurately measure the level of settled out sludge. Jar 42 rests on a platform 46 which is secured to a shaft 48 and rotated by a motor in a jar positioner 50. At the conclusion of the test, jar 42 is tilted by positioner 50 to drain into drain pan 52. In the tilted position water is directed into the jar 42 through a nozzle 54 to clean out the jar in preparation for the subsequent test. The measurement of the interface level between the clear supernatant liquid and the settled sludge is measured optically by means of a photo transistor sensing device 60 which measures infrared or other frequency light transmitted through jar 42 from a source 58. A rack and pinion drive 62 operates in conjunction with a stepping motor 64 to slowly lower the probe 60 from an uppermost zero position, determined by a limit switch 66, until the change in transmitted light indicates that the top of the sludge layer has been reached. An electronic computing system knows the distance traveled by detector 60 in comparison to the known total height of the jar and thus calculates the settled position of the activated sludge.

In the preferred embodiment, measurement of the sludge interface is taken at 5 minute intervals for the first 30 minutes and at 10 minute intervals for the last 30 minutes of the test and the results printed out on printer 38 in the form of a graph which the plant operator can examine at his convenience. It would of course be equally possible to use the measurement directly to develop a control signal which varies the quantities of return sludge and waste discharged from the final settling tank 16.

Turning to FIG. 3 the other half of the testing apparatus is shown. Mounted on the console 40B is a conventional centrifuge 68 which contains a number of test tubes 70 positioned for rotation therein. In the center of the rotor of the centrifuge is a code disk 92 which permits the system to determine the position of the centrifuge by means of a light emitting diode 93 and a photo transistor 94 which are mounted on a cover 95 which is positioned over the centrifuge during operation. Thus, the electronic computing means in the system can determine which test tubes are being measured, filled, or washed. The actual positioning of the test tubes is accomplished electronically by pulsing the drive motor of the centrifuge and comparing the desired position to the actual position as measured by the binary code disk 92 and the photo transistor 94. To clean each test tube after a test has been completed a vaccum probe 72 is pushed downward by an air cylinder 78 through an opening 96 in cap 95 to extract the contents from the test tube. Simultaneously therewith a mixture of air and water is sprayed into the test tube through a tube 74 mounted to the side of vacuum probe 72. The tube is thoroughly cleaned by the spray which is then extracted through vacuum tube 76. The test sample is introduced into the test tubes by another probe 84 which is lowered by an air cylinder 86. The test sample flows in through tube 85 and again a suitable hole is provided in cap 95 to allow probe 84 to enter the test tube. Since an initial purge step is necessary during which fluid in line 85 is removed to ensure that the sample being tested is from a new batch, a suitable cup shaped drain 90 is moved under probe 84 by means of an air cylinder 88. This allows the purged fluid to be directed to a drain rather than into the test tube for the first few minutes of the purging operation. After a test tube has been filled, the centrifuge is run for a period of about 15 minutes causing the solids to precipitate to the bottom of the tube 70. At this time a third probe 83 is lowered through a hole in cap 95 to take an optical measurement of the interface between the clear fluid and the settled solids. A zero position determined by a limit switch 81 is used as a starting point for the measurement. Again, a stepping motor 82 lowers probe 83 through a known distance until the light from a diode source 79 is no longer detected by a photo transistor 80. This indicates the interface between the light blocking solids in the bottom of the test tube and the clear fluid above. Again a ratio is calculated by a computer and the information printed out in the form of a graph by printer 38.

Figure 4:
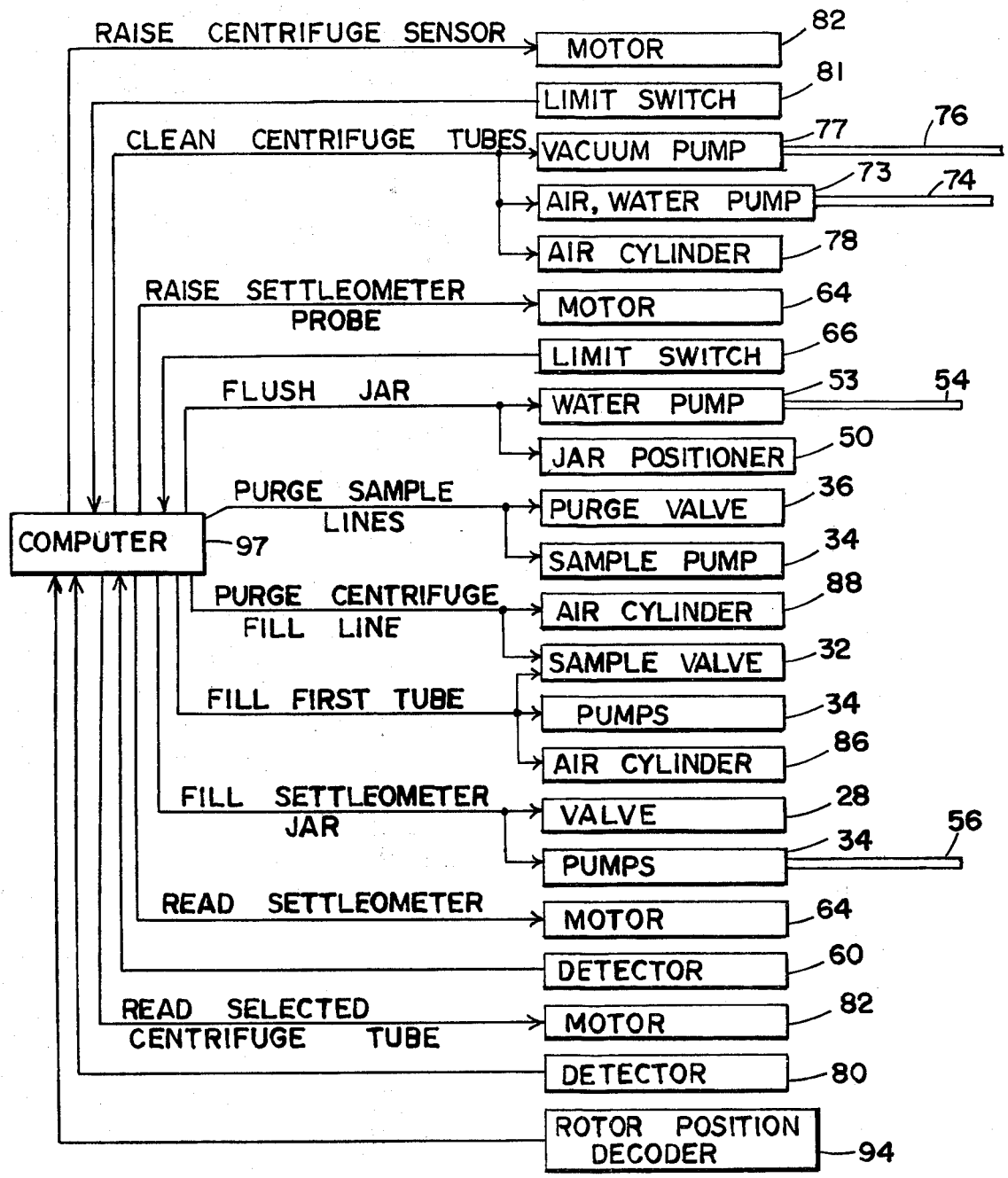
FIG. 4 is a schematic diagram of the typical sequence of operations effected by the automatic circuits of the present invention.

All measurements, calculations, and program steps are controlled according to a predetermined sequence stored in a computer 97 as shown in FIG. 4. Computer 97 operates in a manner well known to those skilled in the art to carry the testing equipment through a pre-planned series of steps in accordance with an internal clock that repeats the testing procedure throughout the day at set times. It is also contemplated that the present invention could simply be operated on demand by a start signal delivered to computer 97. A typical sequence is shown in FIG. 4 with the steps proceeding from top to bottom in a logical but not necessarily the only arrangement. The computer first signals motor 82 to raise the centrifuge sensor probe 83. Limit switch 81 signals the computer when a zero position has been reached. Computer 97 then initiates a cleaning of the centrifuge tubes by activating a vacuum pump 77 which operates through tube 76 and an air and water pump 73 which operates through tube 74. At the same time, air cylinder 78 is operated to move the probe into the test tube. According to its program, the computer raises the settleometer probe by activating motor 64 until limit switch 66 indicates that the probe has reached its uppermost or zero position. Computer 97 then signals the system to flush jar 42 signaling jar positioner 50 to rotate jar 42 into the lowered cleaning position discussed earlier and operating a suitable pump 53 to deliver water through nozzle 54. Before introducing samples for measurement it is desirable to purge the lines. Thus it is contemplated that computer 97 will send a "purge sample lines" signal to valve 36, sample pumps 34, and the desired sample valve 28, 30, or 32 depending upon which sample is being selected. Likewise, the fill line 85 at the test apparatus of the centrifuge should be purged. Accordingly, the computer 97 next operates air cylinder 88 to push drain cup 90 underneath probe 84 to receive fluid therefrom for a short interval. To fill a test tube the computer 97 operates a suitable pump 34 and a suitable valve, such as sample valve 32, to bring in a sample from aerator 12 to the test tube in centrifuge 68. Air cylinder 86 is also operated to lower probe 84 into the test tube for the filling procedure. In the present invention a metering pump is used so that the amount of fluid delivered to test tube 70 can be accurately controlled which, of course, is essential to the proper determination of the ratio of solids in the test tube.

The settleometer jar is also filled with a "fill settleometer jar" signal from computer 97 which operates valve 32 to permit the mixed liquor to be delivered by the proper sample pump 34 through fill tube 56. At the selected intervals the computer operates motor 64 to slowly lower probe 60 until the change in detected radiation from source 58 indicates that the interface between the sludge and the supernatant fluid has been reached. The computer knows the distance moved by motor 64 and therefore can calculate the ratio of settled sludge. In a similar manner the computer 97 can determine the percent of solids in the test tubes by operating motor 82 until the probe 83 lowers to the point where detector 80 senses the top surface of the layer of solids in test tube 70. Rotor position decoder 94 in conjunction with decoding ring 92 indicates to computer 97 which test tube is being read.

Clearly the exact sequence of the steps is not essential to the proper operation of the invention nor for that matter the precise arrangement of mechanisms shown in FIGS. 2 and 3 and accordingly I do not intend to be limited to the exact embodiments shown except as defined by the appended claims.

I claim:

1. An automatic sludge control system for use in a sewage treatment plant comprising in combination:
electronic control means;
sample pumping means operated by said electronic control means;

a settleometer jar adapted to receive a sample from said sample pumping means;

means to optically detect the interface level in said jar between the settled sludge and the supernatant blanket fluid;

means to empty said jar;

means to clean said jar;

centrifuge means containing a plurality of test tubes therein for rotation under centrifugal force, and adapted to receive a sample from said sample pumping means;

means to optically detect the interface level in said tubes between settled solids and the supernatant blanket fluid;

means to empty said tubes;

means to clean said tubes;

computing means to calculate the amount of settled sludge in said jar and settled solids in said tubes; and output means connected to said computing means for producing a signal indicative of the relative quantity of sludge and solids.

2. The system of claim 1 including a printing means connected to said output means so as to display, in record form, the quantity of sludge and solids over a period of time.

3. The system of claim 1 including a signal loop from said output means to control the waste and return sludge flow so as to automatically control the sewage treatment plant.

4. The system of claim 1 in which said means to empty the jar comprises a support platform under the jar rotatable by a jar positioning means to dump the comtents of the jar in a drain and said jar cleaning means comprises a nozzle positioned to spray water into the jar when the jar is tilted by said platform.

5. The system of claim 1 in which said means to empty the tubes comprises a vacuum probe insertable into said tubes and said means to clean the tubes comprises a water and air spray tube affixed to the side of said vacuum probe.

6. The system of claim 1 in which both optical detection means comprise light sources proximate the jar and tubes and movable light detectors positioned and calibrated to move vertically along side the jar and tubes so as to detect light passing through the jar and tubes from said light sources.

7. The system of claim 1 including a test tube filling means movable by means of an air cylinder into a test tube and connected to said sample pumping means so as to direct a sample into a test tube and also including a drain cup movable into position under the test tube filling means and connected to a drain so as to divert sample from the test tube for an interval to purge the sample pumping means.

8. The system of claim 1 in which said electronic control means comprises a computer operable to sequentially operate the elements of the control system according to a preprogrammed sequence and at predetermined times.

9. The system of claim 8 in which said means to empty the jar comprises a support platform under the jar rotatable by a jar positioning means to dump the contents of the jar in a drain and said jar cleaning means comprises a nozzle positioned to spray water in the jar when the jar is tilted by said platform and in which said means to empty the tubes comprises a vacuum probe insertable into said tubes and said means to clean the tubes comprises a water and air spray tube affixed to the side of said vacuum probe and in which both optical detection means comprise light sources proximate the jar and tubes and movable light detectors positioned and calibrated to move vertically along side the jar and tubes so as to detect light passing through the jar and tubes from said light sources and including a test tube filling means movable by means of an air cylinder into a test tube and connected to said sample pumping means so as to direct a sample into a test tube and also including a drain cup movable into position under the test tube filling means and connected to a drain so as to divert sample from the test tube for an interval to purge the sample pumping means, and further including a printing means connected to said output means so as to display, in record form, the quantity of sludge and solids over a period of time, and including a signal loop from said output means to control the waste and return sludge flow so as to automatically control the sewage treatment plant.

* * * * *